United States Patent

Hack et al.

[11] Patent Number: 6,135,774
[45] Date of Patent: Oct. 24, 2000

[54] DIAGNOSIS AND TREATMENT DEVICE FOR TEETH

[75] Inventors: Alexander Hack, Biberach-Rissegg; Bernd Liebermann, Weingarten, both of Germany

[73] Assignee: Kaltenbach & Voigt GmbH & Co., Biberach, Germany

[21] Appl. No.: 09/052,590

[22] Filed: Mar. 31, 1998

[30] Foreign Application Priority Data

Apr. 3, 1997 [DE] Germany ............ 297 05 934 U

[51] Int. Cl.[7] ............... A61C 5/00; A61C 1/00; A61C 3/00
[52] U.S. Cl. ............... 433/215; 433/29; 606/15; 606/18
[58] Field of Search ............... 433/215, 229, 433/29; 606/15, 18

[56] References Cited

U.S. PATENT DOCUMENTS

| | | | |
|---|---|---|---|
| 4,290,433 | 9/1981 | Alfano | 128/665 |
| 4,611,288 | 9/1986 | Duret et al. | 364/474 |
| 4,849,859 | 7/1989 | Nagasawa | 362/32 |
| 4,940,411 | 7/1990 | Vassiliadis et al. | 433/215 |
| 5,107,516 | 4/1992 | Dressel et al. | 372/109 |
| 5,207,576 | 5/1993 | Vassiliadis et al. | 433/215 |
| 5,306,144 | 4/1994 | Hibst et al. | 433/29 |

FOREIGN PATENT DOCUMENTS

| | | |
|---|---|---|
| 0 091 876 | 10/1983 | European Pat. Off. |
| 0 476 914 | 3/1992 | European Pat. Off. |
| 0 619 100 | 10/1994 | European Pat. Off. |
| 0 712 611 | 11/1994 | European Pat. Off. |
| 30 31 249 C2 | 3/1981 | Germany. |
| 33 45 465 A1 | 6/1985 | Germany. |
| 37 13 512 A1 | 10/1987 | Germany. |
| 89 04 568 U | 8/1989 | Germany. |
| 89 13 027 U1 | 4/1991 | Germany. |
| 40 04 736 A1 | 8/1991 | Germany. |
| 40 15 066 A1 | 11/1991 | Germany. |
| 92 08 617 U | 10/1992 | Germany. |
| 42 00 741 A1 | 7/1993 | Germany. |
| 93 20 739 U | 3/1995 | Germany. |
| 93 17 984 U | 5/1995 | Germany. |
| 44 20 401 A1 | 12/1995 | Germany. |
| 195 33 350 A1 | 5/1996 | Germany. |
| 195 30 847 A1 | 2/1997 | Germany. |
| 297 04 185 U1 | 6/1997 | Germany. |
| 3-130701 | 6/1991 | Japan. |
| WO 94/12116 | 6/1994 | WIPO. |
| WO 95/27446 | 10/1995 | WIPO. |

OTHER PUBLICATIONS

"Remote Biomedical Spectroscopic Imaging of Human Artery Wall", Lasers in Surgery and Medicine 8:1–9 (1988).

Primary Examiner—Nicholas D. Lucchesi
Attorney, Agent, or Firm—Marshall, O'Toole, Gerstein, Murray & Borun

[57] ABSTRACT

The invention relates to a device for the diagnosis of the state of health of tooth tissue, having a first light source (1) for the generation of an excitation radiation (2), which is to be directed via a light conductor arrangement (4) onto a tooth tissue region (6) to be investigated and which excites a fluorescence radiation (7) at the tooth tissue region (6), and having detection means (4b, 10) for the detection of the fluorescence radiation (7). In order on the one hand to improve ease of use for the treating dentist and on the other hand to be able to reliably recognize a diseased tooth region, whereby at the same time the patient should not be subjected to unnecessary ablation processes or the removal of healthy tooth substance, the diagnosis device has a second light source (11) for the generation of a treatment laser radiation, which is likewise to be directed onto the tooth tissue region (6) to be investigated, via a light conductor arrangement. The present invention combines the advantages of the diagnosis of tooth regions (6) through evaluation of the fluorescence radiation (7) excited at the investigated tooth (5) with a treatment laser.

27 Claims, 2 Drawing Sheets

(State of the Art)

DIAGNOSIS AND TREATMENT DEVICE FOR TEETH

The present invention relates to a diagnosis device for tooth tissue in accordance with the preamble of claim 1.

It is known to determine the state of health of teeth, for example the presence of caries, plaque or bacterial infection of teeth, by visual inspection or through the employment of X-rays. However, with a visual inspection, satisfactory results often cannot be achieved, since for example caries at an early stage or at a difficult to inspect tooth region cannot be diagnosed. Although, on the other hand, X-rays have proved to be a very effective means of ascertaining caries attack or other tooth diseases, this method of examination is also not optimal because of the damaging effects of X-rays on human health. There is thus a need for the development of a new technique for enabling the state of health of teeth, in particular the presence of caries, plaque or bacterial infection of teeth, to be ascertained.

There has thus been proposed a contactless diagnosis method for the determination of caries, plaque or bacterial infection in teeth, in which the tooth is irradiated with a virtually monochromatic light source. Due to the irradiation of the tooth with monochromatic light, a fluorescence radiation is excited at the tooth, whereby the fluorescence spectrum manifests clear differences between healthy and diseased tooth regions. On the basis of the detection and evaluation of the fluorescence spectrum of the tooth irradiated in this way, a healthy tooth or tissue region can thus be unambiguously distinguished from a diseased tooth or tissue region. Corresponding dental devices for the recognition of caries, plaque or bacterial infection of teeth are known for example from DE-C2 30 31 249 C2, DE-A1 42 00 741 and DE-U1 93 17 984.

FIG. 3 shows an example of such a known diagnosis device. A light source 1 generates an excitation radiation 2 which is delivered to a light conductor 4 via a coupling lens arrangement 3 and thus is directed onto a region 6 of a tooth 5 to be investigated. Due to the virtually monochromatic excitation radiation 2, a fluorescence radiation 7 is excited at the irradiated tooth region 6, which excitation radiation is for example acquired by a further light conductor 8 and delivered via an (optional) spectral filter 9 to a detection device 10 for the detection and, if applicable, evaluation of the fluorescence radiation 7 of the tooth 5. Through the excitation radiation 2, the fluorescence radiation 7 is brought about over a relatively wide spectral range. By means of the interposition of the spectral filter 9 this wide spectral range of the fluorescence radiation 7 can thus be restricted to particular spectral ranges to be investigated. The detection device 10 shows for example the intensity of the fluorescence radiation 7 so that an observer can directly determine the presence of caries, plaque or bacterial infection by comparison of the intensity with the intensity of a healthy tooth region.

After, for example, the irradiated tooth region 6 has been recognised as carious, this tooth region 6 is correspondingly treated, in order to restore the original state of health of the tooth 5. Thereby, commonly a laser treatment is carried out, in which the carious location of the tooth is treated for example with a pulsed laser beam. For this purpose, along with the above-mentioned diagnosis device, there must thus be provided an additional treatment device, whereby a treating dentist must constantly alternate between the two devices in order on the one hand to check the state of health and on the other hand to be able to initiate an appropriate treatment. In particular, the treating dentist must repeatedly interrupt the laser treatment in order to be able to check the diseased or affected location of the treated tooth with the aid of the diagnosis device, since a laser treatment of a tooth region is only appropriate so long as a diseased tooth region is in fact present. Apart from the fact that for the above-mentioned purpose two separate devices are necessary, which not only increases acquisition costs but also increases space requirements, the above-mentioned procedure is also complex and time consuming for a treating doctor.

Thus, in DE-A1-40 15 066, there is proposed the combination of a treatment laser with a diagnosis apparatus, whereby however the diagnosis apparatus determines the state of health of a tooth region on the basis of so-called differential reflectrometry. Thus, the tooth region to be investigated is continuously irradiated with white light of a xenon lamp and at the same time the light reflected from the irradiated tooth region is detected, whereby the reflection spectrum obtained in this way is divided by the spectrum of a reference sample, by which means influences of lamp variations can be compensated. In a computer there are the typical spectra of tissue kinds to be taken into consideration, so that by means of a comparison of forms between the actually measured spectrum and the previously stored spectra it can be decided whether a diseased or healthy tooth region is present. The white light of the xenon lamp is delivered to the tooth region to be investigated via a light conductor which likewise directs the light of a treatment laser, for example an excimer or solid state laser, onto the tooth region to be investigated. The treatment laser is made free for operation when the investigated tooth region is identified as diseased, in order then to be able to treat the diseased tooth region.

As has been described above, DE-A1-40 15 066 describes only the diagnosis of a tooth region on the basis of so-called differential reflectrometry. The differential reflectrometry functions, however, on the basis of a colour measurement, which is to be carried out in the UV and in the visible wavelength range with the aid of an expensive and sophisticated spectrometer for the detection of the reflection radiation and a lighting device which is also sophisticated, namely the xenon lamp, for the illumination of the tooth to be investigated with white light. Differential reflectrometry can, however, be easily affected by environmental light influences. Further, with differential reflectrometry there appears the problem that colour differences of various substances are often of the same order of magnitude as those of examples of the same substance, whereby the selectivity of the diagnosis device is strongly affected. A further problem is the high outlay in terms of time for the spectral evaluation of the reflection spectrum, whereby for example on-line monitoring is made difficult.

From EP-A1-0 619 100 there is likewise known the combination of a diagnosis device with a treatment laser working in the UV wavelength range. In accordance with this publication, the diagnosis of the investigated tooth region is however effected in that the different noises appearing upon ablation of a healthy and a diseased tooth region are evaluated. Likewise it is proposed that the tooth material removed by the treatment laser be investigated and, if appropriate, to control the treatment laser in dependence upon the composition of the tooth material. In the process described in EP-A1-0 619 100, however, in particular the minimal efficiency of the material removal by means of the treatment laser is problematic, as also is the ease with which the evaluation can be influenced by the energy density at the tooth to be investigated, or by a spray which may have been delivered or by environmental noise.

Finally, from WO 95/27446, there is likewise known the combination of a diagnosis device with a treatment device for teeth, whereby the acoustic impulses occurring upon the interaction of the treatment laser impulse with the treated tooth tissue are registered and monitored with regard to a particular peak amplitude. In dependence upon the height of the peak amplitude the kind of tooth region being treated in each case can be determined and if appropriate the radiation energy of the treatment laser can be adapted to the thus determined kind of tissue. In this manner, the danger of subjecting the patient to laser damage in the treatment can be reduced. As with EP-A1-0 619 100, a diagnosis of the tooth region to be treated is however not possible without activation of the treatment laser and corresponding action on the tooth region to be investigated. The further problems mentioned in relation to EP-A1-0 619 100 also appear with this process.

Thus, it is the object of the present invention to so constitute a diagnosis device of the kind mentioned in the introduction that on the one hand the ease of use for a treating dentist is improved and on the other hand a diseased tooth region can be reliably recognised.

In particular it should thereby be avoided that a patient is subjected to unnecessary ablation processes or that healthy tooth substance is removed for the recognition of the tissue condition.

In accordance with the invention, the above-mentioned object is achieved by means of a device according to the claims.

The present invention combines the advantages described above of the diagnosis of tooth regions by evaluation of the fluorescence radiation excited at the investigated tooth, with a treatment laser. The excitation radiation and the treatment laser radiation are preferably delivered to the tooth region to be investigated or treated via one and the same light conductor arrangement, whereby advantageously the treatment laser radiation is activated only after recognition of a diseased tooth region. Separate light conductors for the excitation and treatment laser radiation are likewise possible. Further, there is the possibility of delivering the treatment laser radiation to a handpiece in which this radiation is further directed onto the tissue to be investigated, and to generate the excitation radiation in this handpiece and also to integrate therein the detection of the fluorescence radiation or to direct the fluorescence radiation to the base apparatus.

The fluorescence radiation excited at the tooth region is acquired and evaluated. After recognition of a diseased tooth region, the user can selectively switch in the treatment laser. Alternatively, it can also be provided that the device itself effects the evaluation of the fluorescence radiation and automatically activates the treatment laser when a diseased tooth issue has been recognised. The threshold signal level which is predetermined for the differentiation between a diseased and a healthy tooth tissue may be definable by the person effecting the treatment.

The combination of a treatment laser with a detection of fluorescence radiation was previously not known. The device proposed in accordance with the invention has, however, in particular the advantages that it is simply constructed and further, with regard to the above-mentioned state of the art, exhibits a significantly improved reliability of detection. Further, in contrast to EP-A1-0 619 100 and WO 95/27446, for the diagnosis of a tooth region to be investigated an ablation, i.e. a removal of material, at the investigated tooth need not initially occur. In particular, the employment of the device in accordance with the invention is advantageous for the control of the removal of concretions within the scope of a parodontal therapy, since the fluorescence radiation excited at concretions manifests great differences with regard to healthy tooth regions, so that a selectivity of the removal of concretions can be attained with substantially improved operational reliability.

Along with the above described advantages it is further ensured that a treating dentist can carry out both a diagnosis and also a treatment of teeth or tooth tissues with a single device. By means of simple switching in of the treatment laser, for example with the aid of a foot switch or a switch arranged in a hand apparatus, the treatment laser can be selectively directed onto a tooth region together with the excitation radiation for the excitation of the fluorescence spectrum. Through continuous monitoring of the fluorescence spectrum excited at the simultaneously treated tooth region, the dentist can continuously determine whether the state of health of the tooth has been restored.

In contrast to the above-described state of the art, which likewise combines a diagnosis device with a treatment laser, in accordance with the present invention no reflection radiation is evaluated, rather the fluorescence radiation excited at the irradiated tooth tissue is evaluated, whereby the accuracy of diagnosis is increased.

The subclaims describe further advantageous configurations of the present invention.

The invention will be described below in more detail with reference to a preferred exemplary embodiment.

FIG. 1 shows a preferred exemplary embodiment of the device in accordance with the invention.

Figure 1:
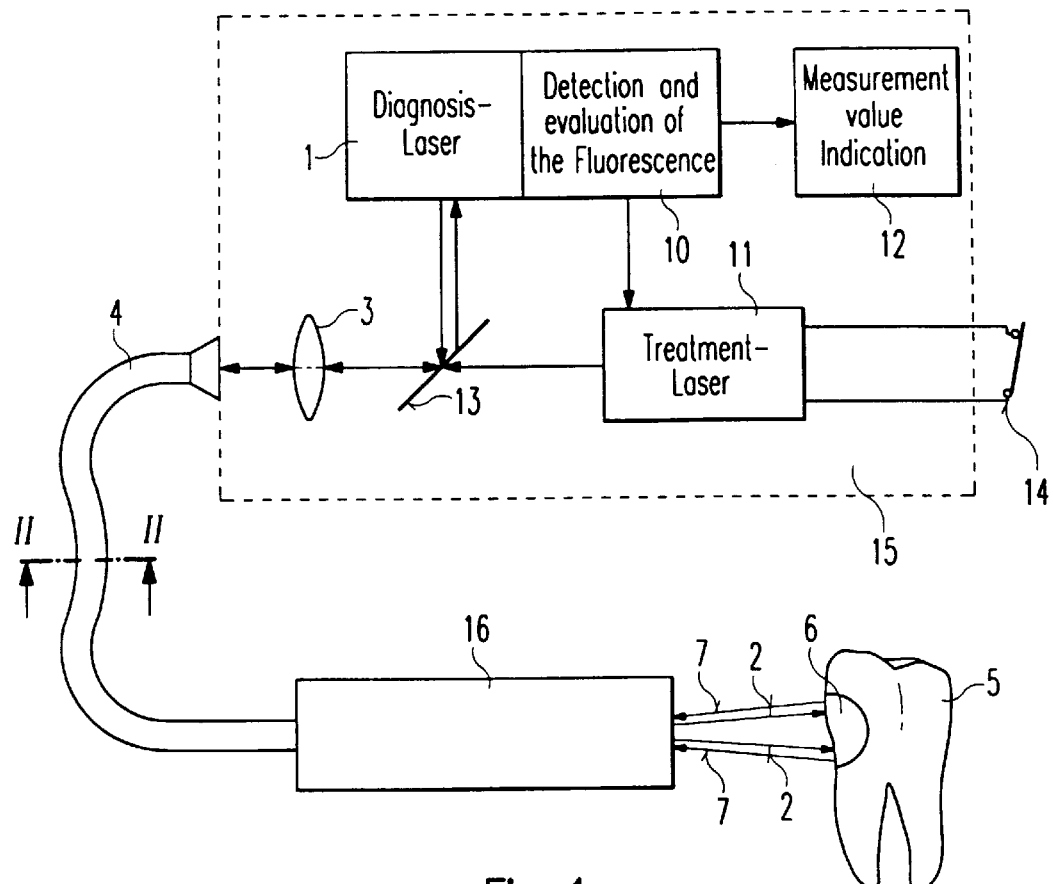
FIG. 1 shows the in principle construction of a preferred exemplary embodiment of the present invention.

In accordance with FIG. 1 the device in accordance with the invention includes a base apparatus 15, which contains a diagnosis laser light source 1. This diagnosis laser light source 1 generates a substantially monochromatic light, whereby the light radiation emitted from the diagnosis laser light source 1 may also exhibit a small bandwidth, of for example 70 nm. The radiation generated by the diagnosis laser light source 1 serves as excitation radiation which excites a fluorescence radiation at a tooth region 6 of a tooth 5 to be investigated, which fluorescence radiation—as will be described below—is evaluated. Trials have shown that with an excitation wavelength range between 600 nm and 700 nm fluorescence radiation is excited at the tooth region 6 irradiated therewith having a wavelength between 650 and 850 nm, whereby with this fluorescence spectrum range a particularly advantageous large separation between the fluorescence intensities to be evaluated of diseased and healthy tooth regions occurs. The fluorescence spectrum appearing with wavelengths in the range between 650 and 850 nm can thus be evaluated in a particularly simple and dependable manner, in order to be able to recognise diseased tooth tissue regions directly on the basis of the detected fluorescence spectrum. An excitation radiation of the diagnosis laser light source 1 in the range between 600 nm and 700 nm is thus particularly advantageous.

As is illustrated in FIG. 1, the excitation radiation generated by the diagnosis laser light source 1 is coupled into a light conductor arrangement 4 via a lens arrangement 3, so that the excitation radiation 2 guided in the light conductor arrangement 4 can be directed onto the desired tooth region 6 of a tooth 5 to be investigated. Fluorescence radiation 7 is excited at the thus irradiated tooth region, which fluorescence radiation is acquired by the light conductor arrangement 4 and delivered back to the base apparatus 15. Via a beam divider 13, in the base apparatus 15 the fluorescence radiation 7 acquired in this way is coupled out and directed to a detection device 10, which for example contains a sensor arrangement for the measurement of the fluorescence radiation. An indicator device 12 is connected with the detection device 10, which indicator device issues the fluorescence radiation intensity measured by the detection device 10 optically or acoustically, so that the treating dentist can, by monitoring this measurement indicator "on-line", i.e. without temporal delay, diagnose the state of health of the investigated tooth region 6, since clear differences appear in the fluorescence spectrum excited at the irradiated tooth region 6 as between diseased and healthy tooth regions. In the case of diseased tooth regions there may be involved for example diseased dentin or tooth enamel affected by caries, concretions, tartar, infected tissue of the root canal, infected mucous membrane of the mouth or infected pulpal tissue.

In general, attention is directed to the fact that by means of evaluation of the fluorescence radiation a reliable diagnosis both of hard and also soft tissue is possible.

Alternatively to the above described configuration, it can also be provided that the detection device 10 itself effects the evaluation of the detected fluorescence radiation and automatically or after preselection of a threshold signal level for differentiation between diseased and healthy tooth regions decides whether the investigated tooth region 6 involves diseased or healthy tooth tissue. In the case of diseased tooth tissue, the detection and evaluation device 10 may for example issue an optical or acoustic warning signal via the indicator device 12. Further, the detection and evaluation device 10 may be combined with the diagnosis laser 1 or integrated therein.

Figure 2:
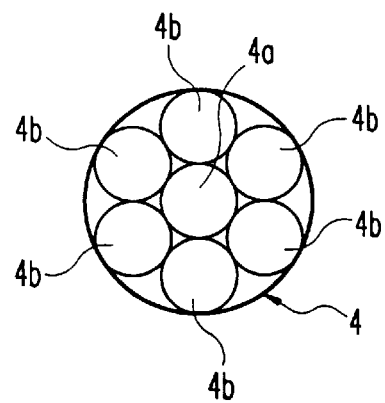
FIG. 2 shows a cross-sectional view of the light conductor arrangement illustrated in FIG. 1, along the broken line shown in FIG. 1.
Figure 3:
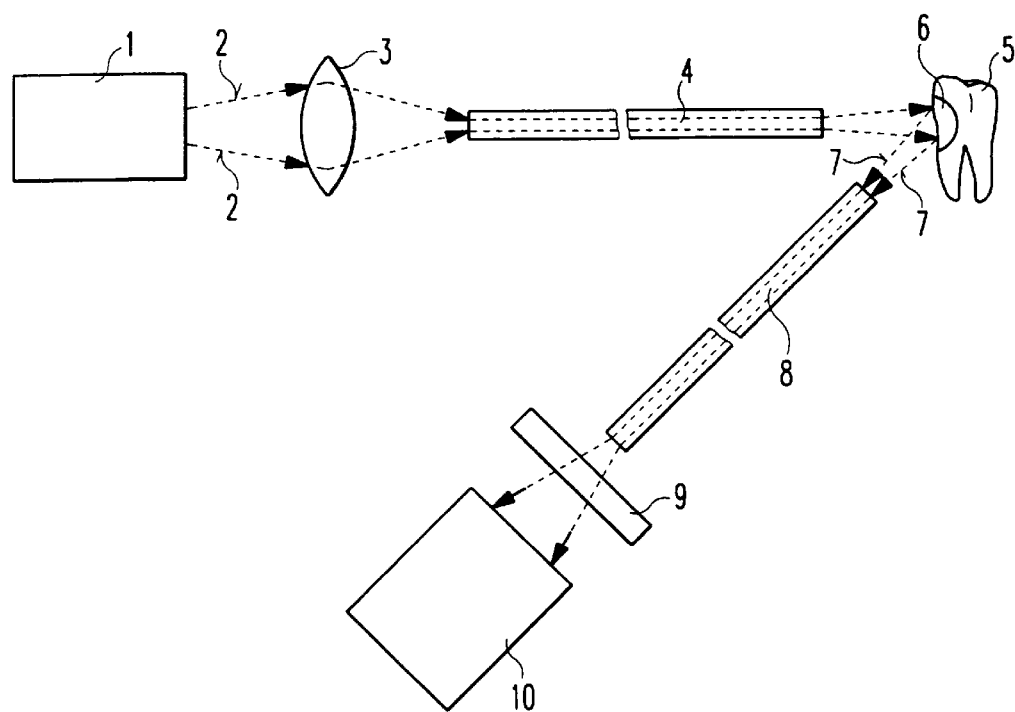
FIG. 3 shows the in principle construction of a known diagnosis device, which evaluates the fluorescence radiation excited at an investigated tooth.

The detection of the fluorescence radiation excited at the tooth region 6 will be explained below with reference to FIG. 2. FIG. 2 shows a cross-sectional view along the broken line of the light conductor arrangement 4 shown in FIG. 1. The light conductor arrangement 4 includes advantageously at least one light conductor fiber 4a for guiding the excitation radiation 2 of the diagnosis laser light source 1 from the base apparatus 15 to the hand apparatus 16. Further, the light conductor arrangement 4 includes at least one further light conductor fiber 4b, which acquires the fluorescence radiation 7 excited at the tooth region 6 and delivers it to the base apparatus 15. The light conductor arrangement 4 can, however, also have a plurality of irradiation light conductor fibers 4a and detection light conductor fibers 4b, arranged alternately with one another. The arrangement illustrated in FIG. 2 is in particular advantageous, wherein a plurality of detection light conductor fibers 4b are arranged concentrically round a single irradiation light conductor fiber 4a, so that in this way the reliability of detection and the accuracy of detection of the detection light conduction fibers 4b, with regard to the fluorescence radiation excited at the tooth region 6, can be increased and stabilized. Advantageously, the diameters of the irradiation light conductor fiber 4a and of the detection light conductors fibers 4b are so selected that by means of the arrangement shown in FIG. 2 there is provided a virtually completely filled cross-sectional area of the light conductor arrangement 4, whereby the detection light conductor fibers 4b are arranged in a closed circle around the single irradiation light conductor 4a.

Alternatively to this, the light conductor fibers for the transmission of the excitation radiation and the fluorescence radiation may be one and the same fiber.

In accordance with the invention, the device has a treatment laser light source 11 combined with the diagnosis laser light source 1, which treatment laser light source may for example be provided by a Er:YAG laser. This treatment laser 11 generates in particular a treatment laser radiation in the infrared region between 2.5 $\mu$m and 3.5 $\mu$m. Upon activation of the treatment laser 11 the treatment laser radiation generated by the treatment laser 11 is likewise guided to the light conductor arrangement 4 via the beam divider 13 and the coupling lens arrangement 3. In particular, the treatment laser radiation, with reference to FIG. 2, is transferred via the same irradiation light conductor fiber 4a as the excitation radiation of the diagnosis laser 1 or via the same fiber which transfers the fluorescence radiation and is directed to the tooth region 6 to be treated, so that within the light conductor arrangement 4 no additional light conductor fibers are needed for the treatment laser radiation. Alternatively, however, there may also be provided additional light conductor fibers within the light conductor arrangement 4 for the transmission of the treatment laser radiation, whereby these additional light conductor fibers are to be so arranged within the handpiece 16 that they are advantageously directed onto the same tooth region 6 which is irradiated with the excitation radiation of the diagnosis laser 1.

For diagnosis of the tooth region 6, initially only the diagnosis laser 1 is operated. After the treating dentist has recognised a diseased tooth region, for example by monitoring the indicator device 12, the dentist can activate the treatment laser 11 by simple actuation of a switch 14, in order for example to remove the disease affected part of the investigated tooth region 6. The switch 14 is advantageously configured as a foot switch so that the treatment laser 11 can be activated and deactivated without the handpiece 16 having to be removed from the tooth region 6. Alternatively, however, the switch 14 may also provided on the handpiece 16, whereby the switch 14 is then to be connected via corresponding electric lines in the light conductor arrangement 4 with the treatment laser 11.

In accordance with the preferred exemplary embodiment shown in FIG. 1 it is however additionally provided that the detection and evaluation device 10 automatically, or after setting of a corresponding decision level by the person effecting the treatment, evaluates the acquired fluorescence radiation 7 of the investigated tooth region 6 and automatically determines the presence or absence of a diseased, for example carious, tooth region. After recognition of a diseased tooth region and actuation of the foot switch 14, the detection and evaluation device 10 automatically controls the treatment laser 11 and activates this in order to treat the investigated tooth region 6 and to remove the disease affected part. Thereby, the detection and evaluation device 10 continues to constantly monitor the fluorescence radiation 7 excited at the treated tooth region 6, so that the detection and evaluation device 10 can continuously determine whether the caries affected part has been able to be removed by means of the treatment laser radiation generated by the laser 11. In this case, via the irradiation light conductor fiber 4a shown in FIG. 2, both the excitation radiation of the diagnosis laser 1 and also the treatment laser radiation of the treatment laser 11 are simultaneously transmitted. As soon as the detection and evaluation device 10 has recognised that the state of health of the treated tooth region 6 has been able to be restored, it deactivates the treatment laser 11.

In accordance with the invention superfluous ablation procedures can thus be avoided at a tooth region 6 to be treated.

The detection and evaluation device 10 can selectively also be arranged directly in the handpiece 16 whereby in this case an appropriate connection of the handpiece 16 with the base apparatus 15 via electric lines would be necessary.

Alternatively to the exemplary embodiment illustrated in FIG. 1, there can be provided for the treatment laser radiation of the treatment laser 11 also a separate light conductor arrangement, which only in the handpiece 16 is combined with the light conductor arrangement 4 for the excitation radiation of the diagnosis laser 1, and thus directed onto the same tooth region 6.

What is claimed is:

1. A device for the diagnosis of the state of health of tooth tissue, comprising:

a first light source for the generation of an excitation radiation, the first light source being adapted to a light conductor arrangement to direct the excitation radiation onto a tooth tissue region to be investigated and which excites a fluorescence radiation at the tooth tissue region, detection means for the detection of the fluorescence radiation, evaluation means which evaluates the detected fluorescence radiation and automatically determines the presence of a diseased or healthy tooth tissue region, a second light source for the generation of a treatment radiation, the second light source adapted to the light conductor arrangement to direct the treatment radiation onto the tooth tissue region, and wherein the detection means and the evaluation means continuously determine the state of health of the tooth tissue region while simultaneously the treatment radiation is directed onto the tooth tissue region.

2. The device of claim 1, comprising output means for optically or acoustically issuing the fluorescence radiation intensity detected by the detection means.

3. The device of claim 2, wherein the output means outputs corresponding information to the state of health of the tooth tissue region irradiated with the excitation radiation.

4. The device of claim 1, wherein the evaluation means automatically activates the second light source in the case that the tooth tissue region irradiated with the excitation radiation is recognized as diseased by the evaluation means.

5. The device of claim 1, wherein the evaluation means activates the second light source for only so long as it is determined that a diseased tooth tissue region is present on the basis of the fluorescence radiation.

6. The device of claim 1, comprising switching means for the selective switching on and off of the second light source.

7. The device of claim 6, wherein the switching means comprises a foot switch.

8. The device of claim 1, wherein the detection means includes at least one detection light conductor fiber disposed in the light conductor arrangement.

9. The device of claim 1, wherein the light conductor arrangement has at least one irradiation light conductor fiber for the transmission of both the excitation radiation and the treatment radiation.

10. The device of claim 1, wherein the light conductor arrangement has an irradiation light conductor fiber and a plurality of detection light conductor fibers disposed concentrically around the irradiation light conductor fiber.

11. The device of claim 1, comprising coupling means which (a) couples the excitation radiation and the treatment radiation into the light conductor arrangement and (b) couples the fluorescence radiation out of the light conductor arrangement.

12. The device of claim 11, wherein the coupling means includes a lens arrangement for coupling the excitation radiation and the treatment radiation into the light conductor arrangement and a beam divider arrangement for coupling the detected fluorescence radiation out.

13. The device of claim 1, wherein the light conductor arrangement is disposed at least in part in a dental handpiece.

14. The device of claim 13, wherein the evaluation means is disposed in the handpiece and is electrically coupled with a base aperture which includes the first and second light sources.

15. The device of claim 1, wherein the first light source generates as an excitation radiation a laser radiation having a wavelength in the range 600 nm to 700 nm.

16. The device of claim 1, wherein the second light source is an Er:YAG laser which generates the treatment radiation with a wavelength in the range between 2.5 $\mu$m and 3.5 $\mu$m.

17. A device for the diagnosis of the state of health of tooth tissue, comprising:

a first light source for the generation of an excitation radiation, the first light source being adapted to a light conductor arrangement to direct the excitation radiation onto a tooth tissue region to be investigated and which excites a fluorescence radiation at the tooth tissue region, detection means for the detection of the fluorescence radiation, a second light source for the generation of a treatment radiation, the second light source being adapted to the light conductor arrangement to direct the treatment radiation onto the tooth tissue region, and wherein the light conductor arrangement comprises an irradiation light conductor fiber for the transmission both of the excitation radiation and the treatment radiation and a plurality of detection light conductor fibers for the transmission of the fluorescence radiation, the plurality of detection light conductor fibers being disposed concentrically around the irradiation light conductor fiber.

18. The device of claim 17, wherein the evaluation means automatically activates the second light source in the case that the tooth tissue region irradiated with the excitation radiation is recognized as diseased by the evaluation means.

19. The device of claim 17, wherein the evaluation means activates the second light source for only so long as it is determined that a diseased tooth tissue region is present on the basis of the fluorescence radiation.

20. The device of claim 17, comprising switching means for the selective switching on and off of the second light source.

21. The device of claim 17, comprising coupling means which (a) couples the excitation radiation and the treatment radiation into the light conductor arrangement and (b) couples the fluorescence radiation out of the light conductor arrangement.

22. The device of claim 21, wherein the coupling means includes a lens arrangement for coupling the excitation radiation and the treatment radiation into the light conductor arrangement and a beam divider arrangement for coupling the detected fluorescence radiation out.

23. The device of claim 17, wherein the light conductor arrangement is disposed at least in part in a dental handpiece.

24. The device of claim 23, wherein the evaluation means is disposed in the handpiece and is electrically coupled with a base aperture which includes the first and second light sources.

25. The device of claim 17, wherein the first light source generates as an excitation radiation a laser radiation having a wavelength in the range 600 nm to 700 nm.

26. The device of claim 17, wherein the second light source is an Er:YAG laser which generates the treatment radiation with a wavelength in the range between 2.5 μm and 3.5 μm.

27. A device for the diagnosis of the state of health of tooth tissue, comprising:

a first light source adapted to direct an excitation radiation via a light conductor arrangement onto a tooth tissue region to be investigated, wherein the excitation radiation excites a fluorescence radiation at the tooth tissue region, a detector coupled to the light conductor to detect the fluorescence radiation and to provide a report of the health of the tooth tissue region, a second light source adapted to direct a treatment radiation via the light conductor onto the tooth tissue region simultaneously with the excitation radiation for continuously determining the state of health of the tooth tissue region during application of the treatment radiation; and wherein the light conductor arrangement comprises an irradiation light conductor fiber for the transmission both of the excitation radiation and the treatment radiation and a plurality of detection light conductor fibers for the transmission of the fluorescence radiation, the plurality of detection light conductor fibers being disposed concentrically around the irradiation light conductor fiber.

* * * * *